(12) United States Patent
De Boni

(10) Patent No.: US 8,025,701 B2
(45) Date of Patent: Sep. 27, 2011

(54) USE OF NATURAL DYES FOR COLORING HUMAN HAIR

(75) Inventor: Maxime De Boni, Tokyo (JP)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/445,912

(22) PCT Filed: Oct. 17, 2007

(86) PCT No.: PCT/FR2007/052193
§ 371 (c)(1),
(2), (4) Date: May 5, 2010

(87) PCT Pub. No.: WO2008/047055
PCT Pub. Date: Apr. 24, 2008

(65) Prior Publication Data
US 2010/0306929 A1  Dec. 9, 2010

Related U.S. Application Data

(60) Provisional application No. 60/855,756, filed on Nov. 1, 2006.

(30) Foreign Application Priority Data

Oct. 17, 2006  (FR) ...................... 06 54319

(51) Int. Cl.
*A61Q 5/10* (2006.01)
(52) U.S. Cl. .................. 8/405; 8/435; 8/609; 8/646
(58) Field of Classification Search ............. 8/405, 435, 8/609, 646
See application file for complete search history.

(56) References Cited

U.S. PATENT DOCUMENTS

| | | | | |
|---|---|---|---|---|
| 5,725,603 A | * | 3/1998 | Audousset et al. | 8/405 |
| 6,248,314 B1 | * | 6/2001 | Nakashimada et al. | 424/70.11 |
| 6,635,090 B1 | * | 10/2003 | Andrean et al. | 8/405 |
| 2007/0251024 A1 | * | 11/2007 | Greaves et al. | 8/405 |

FOREIGN PATENT DOCUMENTS

| | | |
|---|---|---|
| EP | 1 022 014 B1 | 7/2000 |
| EP | 1 127 566 B1 | 8/2001 |
| EP | 1 454 613 A1 | 9/2004 |
| FR | 2 543 434 A1 | 10/1984 |
| FR | 2 549 721 A1 | 2/1985 |
| FR | 2 787 707 A1 | 6/2000 |

OTHER PUBLICATIONS

STIC Search Report dated Nov. 9, 2010.*
International Search Report for PCT/FR2007/052193, dated Jan. 5, 2009.
Database CA [Online] Chemical Abstracts Service, Columbus, Ohio, US; Sep. 27, 2006, XP002507683.
STANSFILE: "Orecin" [Online], May 15, 2006, XP002436770.
"Hansen Solubility Parameters of Solvents," Industrial Solvents Handbook, pp. 35-56 (1996).
English language abstract of EP 1 127 566 B1, Aug. 29, 2001.
English language abstract of FR 2 543 434 A1, Oct. 5, 1984.
English language abstract of FR 2 549 721 A1, Feb. 1, 1985.

* cited by examiner

*Primary Examiner* — Eisa Elhilo
(74) *Attorney, Agent, or Firm* — Finnegan, Henderson, Farabow, Garrett & Dunner, L.L.P.

(57) ABSTRACT

The present invention relates to a hair coloring composition containing at least one natural dye, in particular at least one orcein, and at least one particular organic solvent. The invention also relates to a hair coloring method that comprises applying on the fibers a composition containing one or more natural dyes for a duration sufficiently long for obtaining the desired color. The invention thus provides colorings that respect the nature of the hair while offering strong, low-selectivity and resistant nuances.

18 Claims, No Drawings

USE OF NATURAL DYES FOR COLORING HUMAN HAIR

CROSS REFERENCE TO RELATED APPLICATIONS

This application is a national phase application based on PCT/FR2007/052193, filed Oct. 17, 2007, which claims the priority of French Application No. 0654319, filed Oct. 17, 2006, and claims the benefit of U.S. Provisional Application No. 60/855,756, filed Nov. 1, 2006, the content of all of which is incorporated herein by reference in their entirety.

One subject of the invention is the use of natural dyes for coloring human hair.

It is known to dye keratinous fibers, and in particular human hair with dyeing compositions containing oxidation dye precursors, generally called oxidation bases, such as ortho-or para-phenylenediamines, ortho- or para-aminophenols and heterocyclic compounds. These oxidation bases are generally combined with couplers. These bases and these couplers are colorless or weakly colored compounds which, combined with oxidizing substances, may give rise, via a oxidative condensation process, to colored compounds.

This type of coloring by oxidation makes it possible to obtain permanent colorings but it leads to a degradation of the keratinous fibers via the use of oxidizing agents.

Furthermore, it is known to dye keratinous fibers, and in particular human hair, with dyeing compositions containing direct dyes. The conventional dyes which are used are, in particular, dyes of the nitrobenzene, anthraquinone, nitropyridine, azo, azo, xanthene, acridine, azine or triarylmethane type, or natural dyes. These dyes may be non-ionic, anionic, cationic or amphoteric. These dyes which are colored and coloring molecules have an affinity for the keratinous fibers.

These compositions containing one or more direct dyes are applied to the keratinous fibers for a time necessary to obtain the desired coloring, then rinsed.

The colorings which result therefrom are particularly chromatic colorings which are, however, temporary or semi-permanent due to the nature of the interactions which bond the direct dyes to the keratinous fiber, and their desorption from the surface and/or from the core of the fiber are responsible for their low dyeing power and for their poor resistance to washing or perspiration.

Document FR 2 549 721 describes coloring from natural dyes. The hair-dyeing method described in this document however requires a step of pretreatment with metal salts to obtain a good resistance of the resulting coloration.

The object of the present invention is to provide novel compositions for dyeing human hair which respect the nature of the hair and have strong, not very selective and resistant dyes, capable of generating novel strong dyes which may give various shades.

This objective is achieved with the present invention, one subject of which is a composition for coloring keratin fibers, especially the hair, which comprises one or more natural dyes, and one or more organic solvents chosen from alcohols, ethers or esters having a δH value of the Hansen solubility parameter δH less than or equal to 15 MPa$^{1/2}$.

Another subject of the invention is a kit comprising a first anhydrous composition comprising one or more natural dyes and a second aqueous composition, the first and/or the second composition comprising one or more organic solvents chosen from alcohols, ethers or esters having a value of the Hansen solubility parameter δH less than or equal to 15 MPa$^{1/2}$.

Another subject of the invention is a particular method for coloring hair that includes no pretreatment.

The expression "natural dyes" is understood to mean any dye or dye precursor that is naturally occurring and is produced either by extraction (and optionally purification) from a plant matrix optionally in the presence of natural compounds such as ash or ammonia, or by chemical synthesis.

As natural dyes, mention may be made of quinone dyes (lawsone, juglone, etc.), alizarin, purpurin, carminic acid, kermesic acid, purpurogallin, proto-catechaldehyde, indigo, curcumin, spinulosin, various types of chlorophyll and chlorophyllin, orceins, hematein, hematoxylin, brazilin, brazilein, safflower dyes (such as carthamin), flavonoids (morin, apigenidin, sandalwood), anthocyans (such as apigeninidin), carotenoids, tannins, preferably lawsone, juglone, alizarin, purpurin, carminic acid, kermesic acid, purpurogallin, proto-catechaldehyde, indigo, isatin, curcumin, spinulosin, apigenidin, chlorophyllin, sorghum, orceins and cochineal carmine. It is also possible to use extracts or decoctions containing these natural dyes and in particular henna-based extracts.

According to one particular embodiment, the composition of the invention comprises one or more orceins. According to one variant, the composition comprises one or more orceins and one or more additional natural dyes chosen from curcumin, chlorophyllin, isatin, sorghum and cochineal carmine.

Orceins are dyes obtained from an extract of a lichen, especially orchil, and are optionally chemically modified, in particular by the action of ammonia.

The orceins correspond, in particular, to the formula (I) below:

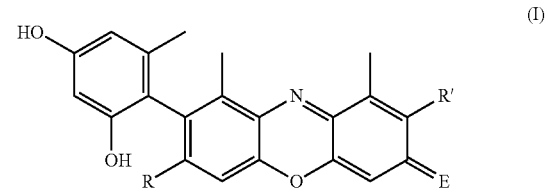

in which R' represents a hydrogen atom, a benzene radical substituted by a hydroxyl or alkyl radical, R represents NH$_2$ or OH and E represents an oxygen atom or an NH radical.

According to one particular embodiment, R' is chosen from hydrogen,

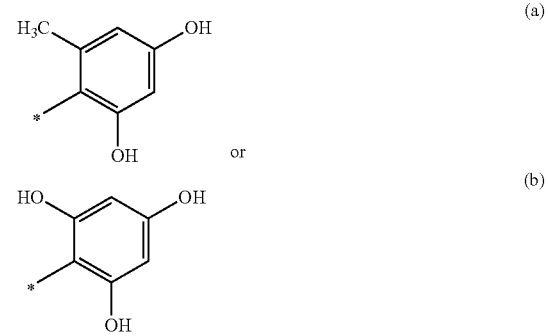

*representing the covalent bond connecting the radical to the rest of the formula (I).

By way of example, mention may be made, for the orceins of formula (I), of α-aminoorcein when R' represents a hydrogen atom, E represents the oxygen atom and R an NH$_2$ radical, α-hydroxyorcein when R' represents a hydrogen atom, E represents the oxygen atom and R a hydroxyl radical.

When R' represents (a), mention may be made of β-aminoorcein when R represents $NH_2$ and E an oxygen atom, β-hydroxyorcein when R represents OH and E an oxygen atom, and β-aminoorceinimine when R represents $NH_2$ and E represents NH.

When R' represents (b), mention may be made of γ-aminoorcein when R represents $NH_2$ and E an oxygen atom, γ-hydroxyorcein when R represents OH and E an oxygen atom, and γ-aminoorceinimine when R represents $NH_2$ and E represents NH. According to one particular embodiment, the orcein used in the present invention is α-hydroxyorcein.

These orceins are described, in particular, in the following articles by H. Musso: Chemische Berichte, 1959, 92, 751-753, Chemische Berichte 1960, 93, 1782-1788, and Chemische Berichte, 1957, 90, 2190-2194.

By way of example of orceins, mention may be made of the product proposed by Panreac under the name ORCEIN DC.

The amount of natural dyes which may be used in the compositions of the invention is generally between 0.001% and 20% by weight of the total weight of the composition, preferably between 0.1 and 10%.

The organic solvent or solvents having a value of the Hansen solubility parameter δH as defined previously are, for example, described in the reference work "Hansen solubility parameters—A user's handbook", Charles M. Hansen, CRC Press, 2000, pages 167 to 185.

This value takes into account the solubility parameter δH linked to the formation of hydrogen bonds. It is recalled that there are three main types of interactions in organic compounds, non-polar interactions, permanent dipole-dipole interactions and hydrogen bonding type interactions, the latter being the subject of the parameter that defines the organic solvent in the present invention.

As examples of a solvent corresponding to this definition, mention may be made of propylene glycol derivatives, benzyl alcohol and alkylene carbonates.

In particular, mention may be made of the following compounds:

| Name | Chemical formula | δH |
|---|---|---|
| Dipropylene glycol methyl ether | $CH_3O[CH_2CH(CH_3)O]_2H$ | 11.2 |
| Tripropylene glycol methyl ether | $CH_3O[CH_2CH(CH_3)O]_3H$ | 10.4 |
| Propylene glycol n-butyl ether (PnB) | $C_4H_9OCH_2CH(CH_3)OH$ | 9.2 |
| Propylene glycol n-propyl ether (PnP) | $C_9H_7OCH_2CH(CH_3)OH$ | 9.2 |
| Dipropylene glycol monomethyl ether acetate | $CH_3COO[CH_2CH(CH_3)O]_2CH_3$ | 8.0 |
| Benzyl alcohol | $C_6H_5CH_2OH$ | 13.7 |
| Ethylene glycol 2-ethylhexyl ether | $C_8H_{17}OCH_2CH_2OH$ | 5.1 |
| 2-pentanol | $CH_3CH(OH)C_3H_7$ | 13.3 |

Preferably, the ethers are alcohol ethers having one or more free alcohol functional groups.

The esters are in particular ether esters.

Preferably, the solvents of the invention are propylene glycol monoethers and benzyl alcohol.

As an alkylene carbonate, mention may be made of the compounds of the following chemical formula:

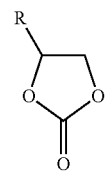

in which R=H, $C_1$-$C_8$ alkyl or $C_1$-$C_4$ hydroxyalkyl.

By way of example, mention may be made of ethylene carbonate (R=H), propylene carbonate (R=$CH_3$), glycerol carbonate (R=$CH_2OH$), or else butylene carbonate (R=$CH_2CH_3$). Among the alkylene carbonates of the invention, propylene carbonate is preferred.

According to one particular embodiment, the δH value is preferably less than 14, preferably less than 12, better still less than 10. According to one particularly preferred embodiment, the value of the component δH is greater than 0. According to one variant, the value of δH is greater than 3, preferably greater than 4.

The composition of the invention generally comprises an amount of organic solvents used in the invention between 0.1 and 80%, preferably between 0.5 and 50% and more preferably still between 1 and 30% of the total weight of the composition.

Preferably, the amount of water is at least equal to 40% relative to the total weight of the dyeing composition. More preferably still, this amount of water is at least equal to 70%.

According to one particular embodiment, the medium suitable for dyeing keratin fibers comprises at least 70% water by weight relative to the total weight of the composition.

The dyeing composition of the invention may contain additional organic solvents that do not correspond to the value of the component δH of the Hansen solubility parameter as defined previously. By way of example, mention may be made of $C_1$-$C_4$ lower alkanols, such as ethanol and isopropanol; polyols such as propylene glycol or glycerol and mixtures thereof.

For dyeing human keratin fibers such as the hair, the dyeing medium is a cosmetically suitable medium.

The total amount of solvents in the composition of the invention may vary between around 0.1 and 80% by weight relative to the total weight of the composition, and more preferably between around 0.5 and 50% by weight and more preferably still between 1 and 30% of the total weight of the composition.

The dyeing compositions may also comprise one or more oxidation dye precursors: one or more oxidation bases and/or one or more couplers. By way of example, the oxidation bases are chosen from para-phenylenediamines, bis-phenylalkylenediamines, para-aminophenols, ortho-aminophenols, heterocyclic bases and addition salts thereof.

The oxidation base or bases present are generally present in an amount ranging from around 0.001 to 20% by weight of the total weight of the dyeing composition, preferably ranging from 0.005 to 6%.

The compositions may contain one or more couplers conventionally used for dyeing keratin fibers. Among these couplers, mention may especially be made of meta-phenylenediamines, meta-aminophenols, meta-diphenols, naphthalene couplers, heterocyclic couplers and also addition salts thereof.

The coupler or couplers are generally present in an amount ranging from about 0.001 to 20% by weight of the total weight of the dyeing composition, preferably ranging from 0.005 to 6%.

Generally, the addition salts of the oxidation bases and of the couplers that can be used in the context of the invention are in particular chosen from the addition salts with an acid such as hydrochlorides, hydrobromides, sulfates, citrates, succinates, tartrates, lactates, tosylates, benzenesulfonates, phosphates and acetates and the addition salts with a base such as sodium hydroxide, potassium hydroxide, ammonium hydroxide, amines or alkanolamines.

The compositions that can be used may also contain one or more additional direct dyes that may, in particular, be chosen from neutral, acid or cationic nitrobenzene dyes, neutral, acid or cationic azo direct dyes, azine direct dyes, triarylmethane direct dyes or indoamine direct dyes.

According to one particular embodiment, the composition of the invention contains, as dyes, only natural dyes.

The compositions that can be used may also incorporate various adjuvants conventionally used in compositions for dyeing hair, such as anionic, non-ionic, cationic, amphoteric or zwitterionic polymers, or mixtures thereof, antioxidants, penetrating agents, sequestering agents, fragrances, buffers, dispersing agents, conditioning agents, film-forming agents, ceramides, preservatives or opacifying agents.

By way of conditioning agent, mention may be made of branched or unbranched, volatile or non-volatile linear or cyclic silicones. These silicones may be in the form of oils, resins or gums, they may in particular be polyorganosiloxanes that are insoluble in the cosmetically acceptable medium.

Organopolysiloxanes are defined in greater detail in the work by Walter Noll, "Chemistry and Technology of Silicones" (1968) Academic Press. They may be volatile or non-volatile.

When they are volatile, the silicones are more particularly chosen from those having a boiling point between 60° C. and 260° C.

By way of conditioning agent, use can also be made of polymers such as the polyquaterniums 22, 6, 10, 11, 35 and 37 and hexadimethrine chloride.

The concentration of conditioning agent(s) in the composition or compositions used in the invention may vary from 0.01 to 10% by weight relative to the total weight of the composition, preferably from 0.05 to 5%, and more preferably still from 0.1 to 3%.

The compositions used in the present invention may contain, in addition, at least one thickening agent also known as "rheology modifiers". This agent may be mineral or organic.

The organic thickening agents may be chosen from fatty acid amides (coconut diethanolamide or monoethanol-amide, oxyethylenated alkyl ether carboxylic acid monoethanolamide), polymeric thickeners such as cellulose thickeners (hydroxyethyl cellulose, hydroxypropyl cellulose, carboxymethyl cellulose), guar gum and its derivatives (hydroxypropyl guar), gums of microbial origin (xanthan gum, scleroglucan gum), homopolymers crosslinked with acrylic acid or acrylamidopropanesulfonic acid and neutral, anionic, amphoteric or cationic associative polymers (polymers comprising hydrophilic zones, and hydrophobic zones having a fatty chain, that are capable, in an aqueous medium, of reversibly associating with one another or with other molecules).

According to one particular embodiment, the thickener is polymeric and is chosen from cellulose thickeners (hydroxyethyl cellulose, hydroxypropyl cellulose, carboxymethyl cellulose), guar gum and its derivatives (hydroxypropyl guar), gums of microbial origin (xanthan gum, scleroglucan gum), homopolymers crosslinked with acrylic acid or acrylamidopropanesulfonic acid.

The compositions used may moreover contain one or more surfactants.

The surfactants suitable for use in the present invention are especially, (i) Anionic Surfactant(s);

By way of example of anionic surfactants that can be used, alone or as mixtures, within the scope of the present invention, mention may especially be made of (non-limiting list) the salts (in particular alkali metal, especially sodium, salts, ammonium salts, amine salts, amino alcohol salts or magnesium salts) of the following compounds: alkyl sulfates, alkyl ether sulfates, alkylamido ether sulfates, alkylaryl polyether sulfates, monoglyceride sulfates; alkyl sulfonates, alkyl phosphates, alkylamide sulfonates, alkylaryl sulfonates, α-olefin sulfonates, paraffin sulfonates; $(C_6$-$C_{24})$alkyl sulfosuccinates, $(C_6$-$C_{24})$alkyl ether sulfosuccinates; $(C_6$-$C_{24})$alkylamide sulfosuccinates; $(C_6$-$C_{24})$alkyl sulfoacetates; $(C_6$-$C_{24})$acyl sarcosinates and $(C_6$-$C_{24})$acyl glutamates. Mention may also be made of $(C_6$-$C_{24})$alkyl polyglycoside carboxylic esters such as alkyl glucoside citrates, alkyl polyglycoside tartrate and alkyl polyglycoside sulfosuccinates, alkyl sulfosuccinamates; acyl isethionates and N-acyl taurates, the alkyl or acyl radical of all these various compounds preferably comprising from 12 to 20 carbon atoms and the aryl radical preferably denoting a phenyl or benzyl group. Among the anionic surfactants that can also be used, mention may also be made of the salts of fatty acids such as the salts of oleic, ricinoleic, palmitic and stearic acids, the acids of coconut oil or of hydrogenated coconut oil; and acyl lactylates of which the acyl radical comprises 8 to 20 carbon atoms. Use may also be made of alkyl D-galactoside uronic acids and salts thereof, polyoxyalkylenated $(C_6$-$C_{24})$alkyl ether carboxylic acids, polyoxyalkylenated $(C_6$-$C_{24})$alkylaryl ether carboxylic acids, polyoxyalkylenated $(C_6$-$C_{24})$alkylamido ether carboxylic acids and salts thereof, in particular those comprising from 2 to 50 alkylene, in particular ethylene oxide groups, and mixtures thereof.

(ii) Non-ionic Surfactant(s):

The non-ionic surfactants are themselves also compounds which are well known per se (in this respect see, in particular, "Handbook of Surfactants" by M. R. Porter, published by Blackie & Son (Glasgow and London), 1991, pp. 116-178). Thus they may especially be chosen from (non-limiting list) alcohols, α-diols or alkylphenols that are polyethoxylated or polypropoxylated, having a fatty chain comprising, for example 8 to 18 carbon atoms, the number of ethylene oxide or propylene oxide groups possibly ranging, in particular, from 2 to 50. Mention may also be made of the copolymers of ethylene and propylene oxide, the condensates of ethylene and propylene oxide with fatty alcohols; polyethoxylated fatty amides preferably having from 2 to 30 mol of ethylene oxide, polyglycerolated fatty amides comprising, on average, 1 to 5, and in particular 1.5 to 4, glycerol groups; oxyethylenated esters of sorbitan fatty acids having from 2 to 30 mol of ethylene oxide; sucrose fatty acid esters, polyethylene glycol fatty acid esters, alkyl polyglycosides, N-alkylglucamine derivatives, amine oxides such as oxides of $(C_{10}$-$C_{14})$ alkylamines or oxides of N-acylamino-propylmorpholine (iii) Amphoteric or Zwitterionic Surfactant(s):

The amphoteric or zwitterionic surfactants may especially be (non-limiting list) derivatives of aliphatic secondary or tertiary amines in which the aliphatic radical is a linear or branched chain comprising 8 to 18 carbon atoms and containing at least one water-solubilizing anionic group (for example carboxylate, sulfonate, sulfate, phosphate or phosphonate); mention may also be made of $(C_8$-$C_{20})$alkyl betaines, sulfobetaines, $(C_8-C_{20})$alkylamido-$(C_1-C_6)$ alkyl betaines or $(C_8-C_{20})$alkylamido$(C_1-C_6)$alkyl sulfobetaines.

Among the amine derivatives, mention may be made of the products sold under the name MIRANOL, as described in U.S. Pat. Nos. 2,528,378 and 2,781,354 and classified in the CTFA dictionary, 3rd edition, 1982, under the names Amphocarboxyglycinates and Amphocarboxypropionates.

These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Capryl-amphodipropionate, Disodium Capryloamphodipropionate, Lauroamphodipropionic acid, Cocoamphodipropionic acid.

By way of example, mention may be made of the cocoamphodiacetate sold under the trade name MIRANOL® C2M concentrate by Rhodia Chimie.

(iv) Cationic Surfactants:

Among the cationic surfactants, mention may, in particular, be made (non-limiting list) of: salts of primary, secondary or tertiary fatty amines, optionally polyoxyalkylenated; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives; or oxides of amines having a cationic nature.

The amounts of surfactants present in the composition used in the process of the invention may vary from 0.01 to 40% and preferably from 0.5 to 30% of the total weight of the composition.

The pH of the composition applied to the fibers is generally between 2 and 13, preferably between 3 and 8. It may be adjusted to the desired value using acidifying or basifying agents commonly used in dyeing keratinous fibers or else using conventional buffer systems.

Among the acidifying agents, mention may be made, by way of example, of mineral or organic acids such as hydrochloric acid, ortho-phosphoric acid, sulfuric acid, carboxylic acids such acetic acid, tartaric acid, citric acid, lactic acid and sulfonic acids.

Among the basifying agents, mention may be made, by way of example, of ammonium hydroxide, alkali metal carbonates, alkanolamines such as mono-, di- and triethanolamines and also their derivatives, sodium or potassium hydroxide and compounds of formula (ii) below:

$$\begin{array}{c} R_a \\ \diagdown \\ N-W-N \\ \diagup \\ R_c \end{array} \begin{array}{c} R_b \\ \diagup \\ \diagdown \\ R_d \end{array} \quad (II)$$

in which W is a propylene residue optionally substituted by a hydroxyl group or a $C_1-C_4$ alkyl radical; $R_a$, $R_b$, $R_c$ and $R_d$, being identical or different, represent a hydrogen atom, a $C_1-C_4$ alkyl radical or a $C_1-C_4$ hydroxyalkyl radical.

When the composition comprises at least one oxidation dye precursor or when it is desired to use a lightening dye, an oxidizing agent may be used.

The oxidizing agents conventionally used for oxidation dyeing of keratinous fibers are, for example, hydrogen peroxide, urea peroxide, alkali metal bromates, persalts such as perborates and persulfates, peracids and oxidase enzymes, among which mention may be made of peroxidases, 2-electron oxidoreductases such as uricases and 4-electron oxygenases such as laccases. Hydrogen peroxide is particularly preferred.

This oxidizing agent may also be present in the composition used in the invention or applied independently in the form of an oxidizing composition.

The oxidizing composition may also incorporate various adjuvants conventionally used in compositions for dyeing hair and as defined previously.

According to the invention, the leave-in time of the compositions is generally between 1 minute and 1 hour.

The process of the invention which consists in applying, to human hair, a composition comprising one or more natural dyes, in particular orcein(s), may be carried out at a temperature varying between ambient temperature (20-25° C.) and 200° C., preferably between ambient temperature and 60° C.

The process of the invention may comprise a subsequent rinsing step, or other later steps such as a step for conditioning, hair shaping, etc.

According to one particular embodiment, the method of the invention is implemented without pretreatment with metal salts, in particular without pretreatment with salts of copper, zinc, aluminum, etc.

According to another particular embodiment, the method of the invention is a hair-dyeing method that comprises, as the only steps, the application of a composition comprising at least one natural dye to the hair for a sufficient time to obtain the desired coloring, optionally followed by a rinsing step.

The kit of the invention comprises a first composition comprising one or more natural dyes in anhydrous form and a second aqueous composition, the first and/or the second composition comprising one or more organic solvents chosen from alcohols, ethers or esters having a value of the Hansen solubility parameter δH less than or equal to 15 MPa$^{1/2}$.

According to one particular embodiment of the kit, the composition comprising the natural dye or dyes, in particular the orcein or orceins, is in powder form. By way of example, these dyes are in the form of a powder mixed with spruce sawdust.

According to one particular embodiment, the method is implemented starting from a composition comprising one or more orceins.

According to another embodiment, the natural dye or dyes, especially the orcein or orceins, are in the form of an anhydrous liquid in which the dye or dyes are dissolved or dispersed. According to one variant, the anhydrous liquid used in the present invention is, for example, composed of organic solvents used in the composition of the invention.

At the time of use, the anhydrous composition is mixed with the second composition to form a ready-to-use composition. Such a ready-to-use composition is obtained with remarkable ease of mixing and makes it possible to obtain a particularly uniform coloring on the hair from the tip to the root of the hair.

The examples that follow are used to illustrate the invention without however being limiting.

EXAMPLES

Example 1

A composition comprising 5% of benzyl alcohol, 15% of ethanol, 0.2% of benzoic acid, 1.6% of hydroxyethyl cellulose, water (qs for 100) and 0.5% of α-hydroxyorcein was applied at ambient temperature, for 20 minutes, to a lock of natural hair having 90% of white hair and to a lock of permed hair having 90% of white hair.

After the application, the locks were rinsed, shampooed and dried. They were colored dark purple in a strong and not very selective manner, that is to say that visually the coloring obtained with the natural hair and the permed hair were very close. A series of 12 washes applied to the two types of locks led to a slight degradation of the coloring (less than 10%).

Example 2

A composition comprising 5% of benzyl alcohol, 15% of ethanol, 0.2% of benzoic acid, 2% of ammonium hydroxide, 1.6% of hydroxyethyl cellulose, water (qs for 100) and 0.5% of α-hydroxyorcein was mixed weight for weight with an oxidizing formulation of hydrogen peroxide having a titer of 20 volumes of aqueous hydrogen peroxide. This mixture was applied at ambient temperature, for 30 minutes, to a lock of natural hair having 90% of white hair and to a lock of permed hair having 90% of white hair.

After application, the locks were rinsed, shampooed and dried. They were strongly colored dark purple. The colorings were very homogeneous.

Example 3

The following dyeing composition was prepared (contents expressed in grams of active material):

| | |
|---|---|
| Curcumin | 0.4 |
| Isatin | 0.4 |
| Orcein | 0.2 |
| Propylene carbonate | 10 |
| Ethanol | 10 |
| Hydroxyethyl cellulose (MW 1 300 000) | 1.5 |
| Citric acid | qs for pH 3 |
| Demineralized water | qs for 100 |

This composition was applied, on the one hand, to locks of natural gray hair having 90% of white hair and, on the other hand, to locks of permed gray hair, having 90% of white hair, for 30 minutes at ambient temperature.

At the end of the waiting time, the locks were rinsed, shampooed then rinsed and dried. They were dyed a sparingly selective mahogany shade.

Example 4

The following dyeing composition was prepared (contents expressed in grams of active material):

| | |
|---|---|
| Copper chlorophyllin | 0.1 |
| Indigo | 0.5 |
| Orcein | 0.1 |
| Curcumin | 0.3 |
| Propylene carbonate | 10 |
| Ethanol | 10 |
| Hydroxyethyl cellulose (MW 1 300 000) | 1.5 |
| Citric acid | qs for pH 3 |
| Demineralized water | qs for 100 |

This composition was applied, on the one hand, to locks of natural gray hair having 90% of white hair and, on the other hand, to locks of permed gray hair, having 90% of white hair, for 30 minutes at ambient temperature.

At the end of the waiting time, the locks were rinsed, shampooed then rinsed and dried. They were dyed a uniform chestnut shade.

Example 4

Comparative

The following compositions were produced (amounts expressed in g %)

| | A (invention) | B (comparative) |
|---|---|---|
| Benzyl alcohol | 5 | — |
| Ethanol | 15 | 20 |
| Benzoic acid | 0.2 | 0.2 |
| Hydroxyethyl cellulose | 1.6 | 1.6 |
| Orcein DC (PANREAC FRANCE) | 0.5 | 0.5 |
| Water | qs for 100 | qs for 100 |

Each composition was applied to locks of natural hair having 90% white hair (NW), and to locks of sensitized hair (41.6% alkaline solubilities).

Each lock treated was subjected to various waiting times:
waiting time of 20 min at ambient temperature;
waiting time of 30 min at ambient temperature.

The locks were then rinsed, washed with a standard shampoo and dried.

The dyeing of the hair was evaluated in the L*a*b* system with a Minolta CM2600-d® spectrophotometer. In this system, L represents the intensity and the lower the value of L*, the more intense the coloring obtained.

| | | L* |
|---|---|---|
| NW hair | Comp A/20 min | 28.15 |
| | Comp B/20 min | 47.81 |
| 41.6 AS hair | Comp A/20 min | 26.69 |
| | Comp B/20 min | 44.49 |
| NW hair | Comp A/30 min | 27.51 |
| | Comp B/30 min | 45.07 |
| 41.6 AS hair | Comp A/30 min | 27.56 |
| | Comp B/30 min | 42.59 |

Composition A according to the invention has lower L* values than composition B, both for a waiting time of 20 min and 30 min. On the two types of hair treated and for the two waiting times, the color obtained is darker, more powerful with the composition of the invention, composition A, comprising an organic solvent having a value of the δH parameter less than 15 (benzyl alcohol: value of δH=13.7) than with a composition containing ethanol for which the value of δH is 19.4).

Example 6

Comparison of the Method with Pretreatment/without Pretreatment

Pretreatment Composition C (in g %)

| | C |
|---|---|
| Hydrated aluminum potassium sulfate (AlK(SO$_4$)$_2$•12H$_2$O) | 9.48 (=5.16 as non-hydrated salt |
| Citric acid | qs for pH = 3 |
| Water | qs for 100 g |

On locks of natural hair having 90% of white hair and locks of sensitized hair (41.6% alkaline solubility), the pretreatment composition C was applied with the composition A of the invention according to one of the methods described below.

Method 1 (invention):
  dyeing with composition A
  waiting time 30 min
  rinsing, shampooing, drying
Method 2 (comparative):
  pretreatment with composition C: waiting time 5 min
  rinsing with warm water
  dyeing with composition A: waiting time 30 min
  rinsing, shampooing and drying
Method 3 (invention):
  dyeing with composition A
  waiting time 20 min
  rinsing, shampooing, drying
Method 4 (comparative):
  pretreatment with composition C: waiting time 15 min
  rinsing with warm water
  dyeing with composition A: waiting time 20 min The dyeing of the locks was evaluated as in example 3 by measuring L* in order to evaluate the intensity of the dyeing. The following results were obtained:

|  |  | L* |
|---|---|---|
| NW hair | Method 1 | 27.51 |
|  | Method 2 | 31.66 |
|  | Method 3 | 28.15 |
|  | Method 4 | 31.92 |
| 41.6 AS hair | Method 1 | 27.56 |
|  | Method 2 | 29.56 |
|  | Method 3 | 26.69 |
|  | Method 4 | 35.24 |

The locks dyed according to method 1 or 3 according to the invention have an L* value lower than the locks dyed according to method 2 or 4 with pretreatment with metal salts: the color is darker with a method without pretreatment, this being so for a dyeing waiting period of 20 and 30 min.

Methods 1 and 2 were also carried out on locks of permed hair containing 90% of white hair (PW).

The dyeing was evaluated as described previously in the L*a*b* system. In this system, L represents the intensity, and the lower the L* value, the more intense the coloring obtained. The chromaticity was measured by the values a* and b*, a* representing the red/green axis and b* the yellow/blue axis.

The selectivity of the dyeing, which is representative of the uniformity of dyeing along the fiber, from the tip to the root of the hair, was evaluated according to ΔE, which is the variation in the color between the dyed natural hair and the dyed permed hair, and was obtained from the formula:

$$\Delta E = \sqrt{(L^* - L_o^*)^2 + (a^* - a_o^*)^2 + (b^* - b_o^*)^2}$$

in which L* represents the intensity and a* and b* the chromaticity of the dyed natural hair and $L_o^*$ represents the intensity and $a_o^*$ and $b_o^*$ the chromaticity of the dyed sensitized hair. The lower the value of ΔE, the lower the selectivity and the more uniform the dyeing is along the hair.

The results are collated in the table below:

|  | L* | a* | b* | Selectivity |
|---|---|---|---|---|
| NW method 1 | 27.51 | 14.06 | 1.83 | 3.30 |
| PW method 1 | 24.24 | 14.42 | 1.61 |  |
| NW method 2 | 31.66 | 14.81 | 3.27 | 8.59 |
| PW method 2 | 23.36 | 12.92 | 4.44 |  |

The homogeneity of the dyeing is much more uniform with the method of the present invention without pretreatment.

The invention claimed is:

1. A dyeing composition comprising at least one natural dye chosen from orceins, alizarin, purpurin, carminic acid, kermesic acid, purpuroqallin, protocatechaldehyde, indigo, curcumin, spinulosin, apiqenidin, chlorophyllin, sorghum, and cochineal carmine and at least one organic solvent having a value of the Hansen solubility parameter δH less than or equal to 15 MPa$^{1/2}$ chosen from alcohols, ethers and esters.

2. The dyeing composition according to claim 1, wherein the at least one natural dye is chosen from orceins.

3. The dyeing composition according to claim 2, further comprising at least one natural dye chosen from curcumin, chlorophyllin, sorghum, and cochineal carmine.

4. The dyeing composition according to claim 2, wherein the orceins are chosen from orceins of formula (I) below:

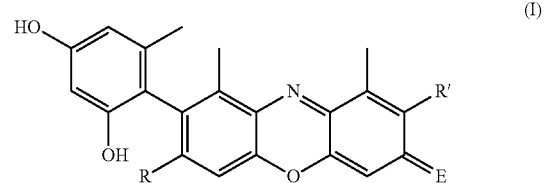

wherein
  R' is chosen from hydrogen and benzene radicals substituted by a hydroxyl or alkyl radical,
  R is NH$_2$ or OH, and
  E is oxygen or an NH radical.

5. The dyeing composition according to claim 4, wherein R' is chosen from hydrogen and radicals chosen from:

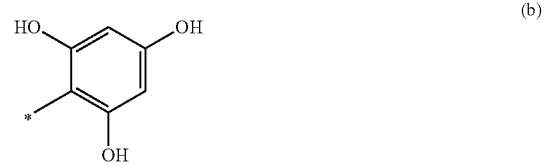

wherein * represents a covalent bond connecting the radical to the rest of formula (I).

6. The dyeing composition according to claim 2, wherein the orceins are chosen from α-aminoorcein and α-hydroxyorcein.

7. The dyeing according to claim 2, wherein the orceins are chosen from β-aminoorcein, β-hydroxyorcein, and β-aminoorceinimine.

8. The dyeing composition according to claim 2, wherein the orceins are chosen from γ-aminoorcein, γ-hydroxyorcein, and γ-aminoorceinimine.

9. The dyeing composition according to claim 2, wherein the orcein is α-hydroxyorcein.

10. The dyeing composition according to claim 1, wherein the at least one natural dye is present in an amount ranging from 0.001% to 20% by weight relative to the total weight of the dyeing composition.

11. The dyeing composition according to claim 1, further comprising at least one surfactant.

12. The dyeing composition according to claim 1, wherein the at least one organic solvent is chosen from propylene glycol ethers, benzyl alcohol, and alkylene carbonates.

13. The dyeing composition according to claim 12, wherein the alkylene carbonates are chosen from ethylene carbonate, propylene carbonate, glycerol carbonate, and butylene carbonate.

14. The dyeing composition according to claim 1, wherein the dyeing composition comprises at least 70% water.

15. The dyeing composition according to claim 1, further comprising at least one thickening polymer.

16. A kit comprising a first anhydrous composition comprising at least one natural dye chosen from orceins, alizarin, purpurin, carminic acid, kermesic acid, purpurogallin, protocatechaldehyde, indigo, curcumin, spinulosin, apigenidin, chlorophyllin, sorghum, and cochineal carmine and a second aqueous composition, wherein at least one of the first and second compositions comprises at least one organic solvent chosen from alcohols, ethers, and esters having a value of the Hansen solubility parameter δH less than or equal to 15 $MPa^{1/2}$.

17. A method of dyeing human hair comprising:
applying to the hair, without pretreatment, a composition comprising at least one natural dye chosen from orceins, alizarin, purpurin, carminic acid, kermesic acid, purpurogallin, protocatechaldehyde, indigo, curcumin, spinulosin, apigenidin, chlorophyllin, sorghum, and cochineal carmine, and at least one organic solvent having a value of the Hansen solubility parameter δH less than or equal to 15 $MPa^{1/2}$ chosen from alcohols, ethers, and esters, for a sufficient time to obtain the desired coloring; and optionally rinsing the hair.

18. The method of claim 17, wherein the at least one natural dye is chosen from orceins.

* * * * *